United States Patent [19]

Bishop

[11] 3,968,195

[45] July 6, 1976

[54] METHOD FOR MAKING STERILE CONNECTIONS

[76] Inventor: Marilyn Bishop, One N. 341 Indian Knoll Road, West Chicago, Ill. 60185

[22] Filed: June 17, 1974

[21] Appl. No.: 479,755

[52] U.S. Cl. .............................. 264/154; 128/214 D; 156/82; 156/304; 264/248
[51] Int. Cl.$^2$ ......................................... B29C 27/00
[58] Field of Search .......................... 264/248, 154; 128/214.2, 214 D; 156/82, 304; 65/57, 120

[56] References Cited
UNITED STATES PATENTS

| | | | |
|---|---|---|---|
| 1,701,541 | 2/1929 | Ray | 65/57 |
| 2,839,788 | 6/1958 | Dembiak | 264/310 |
| 2,950,716 | 8/1960 | Bellamy, Jr. et al. | 128/214 D |
| 3,404,051 | 10/1968 | Hall | 156/304 |
| 3,467,095 | 9/1969 | Ross | 128/214.2 |
| 3,616,024 | 10/1971 | Windle | 156/304 |

FOREIGN PATENTS OR APPLICATIONS

| | | | |
|---|---|---|---|
| 1,300,635 | 8/1969 | Germany | 128/214 R |

Primary Examiner—Robert F. White
Assistant Examiner—T. E. Balhoff
Attorney, Agent, or Firm—Henry L. Brinks; Jerold A. Jacover

[57] ABSTRACT

A method for making a sterile connection between fluid passage means such as a port structure for passing sterile fluids or other biological material, is disclosed. The port structure includes a flexible sleeve having a rigid thermoplastic tube secured therein. The outer surface of the sleeve has greater thermoplastic properties than the inner surface, enabling the sleeve to be heat sealed to the fluid passage means without sealing off the inner surface. The rigid tube has a free end extending outside the sleeve, having a thermoplastic diaphragm which seals off the free end. When a sterile connection between two fluid passage means incorporating the port structure is desired, the free ends of each rigid tube are aligned and softened, and each thermoplastic diaphragm is opened. The free ends of the rigid tubes are then brought into contact and held in position under a slight pressure while the thermoplastic tubes cool and solidify, thereby creating a permanent connection.

14 Claims, 7 Drawing Figures

U.S. Patent July 6, 1976 3,968,195
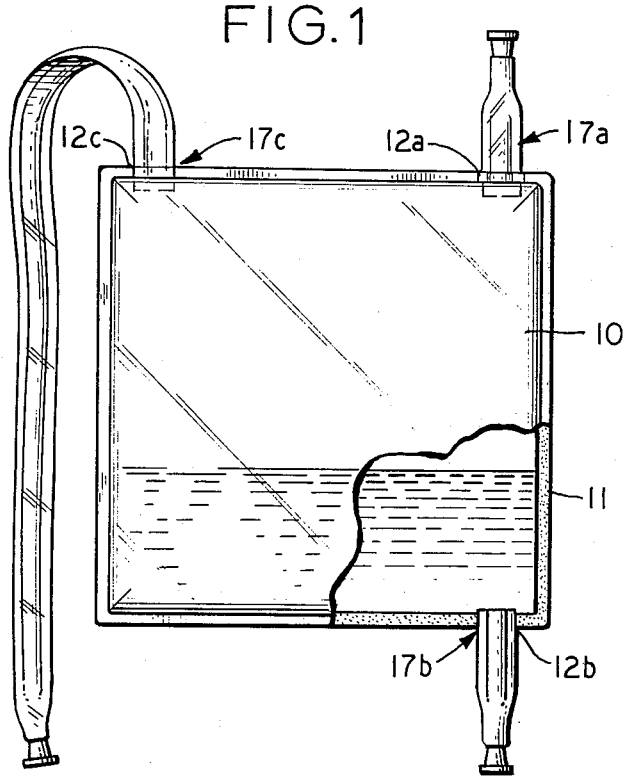
FIG. 1
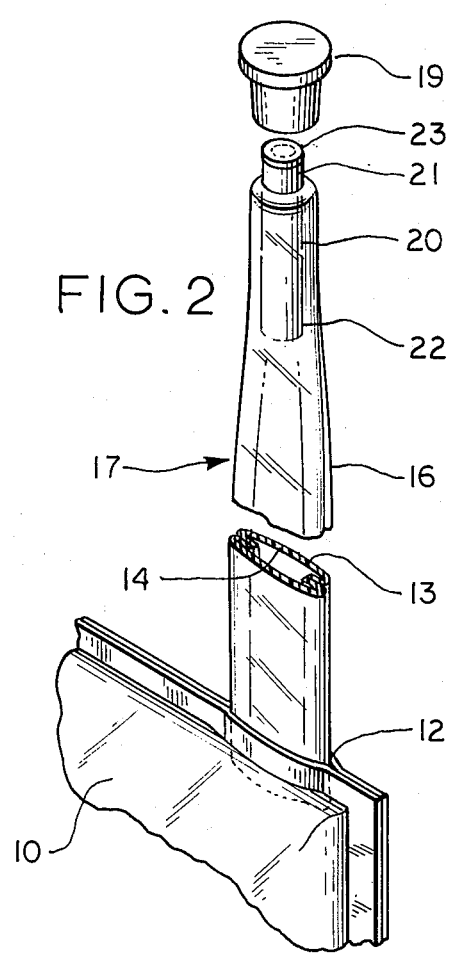
FIG. 2
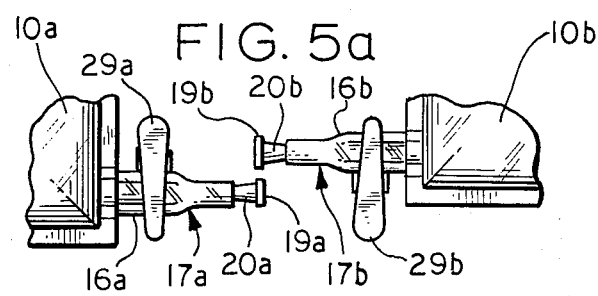
FIG. 5a
FIG. 5b
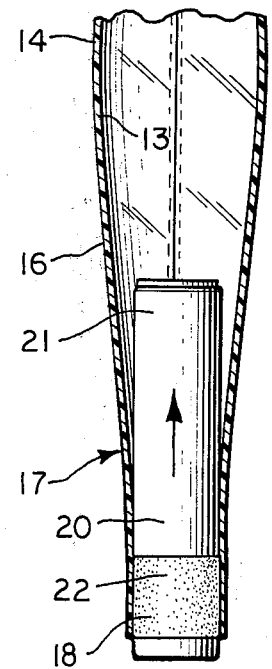
FIG. 3
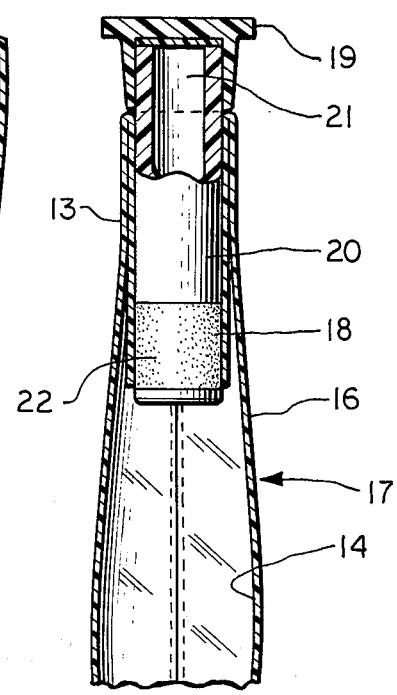
FIG. 4
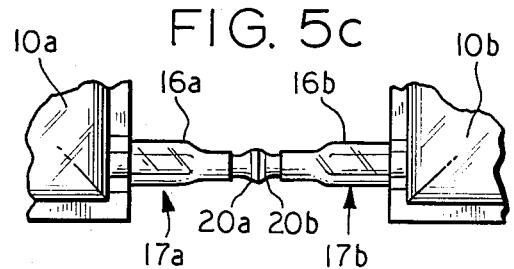
FIG. 5c

METHOD FOR MAKING STERILE CONNECTIONS

BACKGROUND OF THE INVENTION

This invention relates to a port structure used with containers for holding or passing sterile fluids or biological materials. The invention further relates to a method for making sterile connections between two containers by utilizing specific features of the port structure which is described in greater detail hereinafter.

At the present time there are numerous medical and scientific practices which require the sterile transfer of fluids or other biological materials from one container to another. The state of the art is such, however, that no true sterile method for joining separate containers to facilitate the sterile transfer of fluids is available. Thus, where a sterile transfer from one container to another is required, it is often accomplished by prejoining the containers together and then sterilizing the entire assembly. This method is not entirely satisfactory because it necessitates the handling of cumbersome prejoined units, and involves additional costs associated with prejoined containers.

When prejoined units are impracticable, separate containers are generally connected by means of a sterile transfer set. Such a transfer set includes a pair of plastic couplers which are adapted to pierce and penetrate the corresponding containers to be joined. Once the transfer set is removed from its sterilized package, however, the plastic couplers are susceptible to contamination from airborne bacteria. As a result, a sterile connection cannot be assured. Moreover, as a general rule, a sterile transfer set can be correctly used only by persons who have had proper training.

The method and apparatus of the invention achieves a true sterile connection which can be accomplished with only a minimal amount of training and skill. More particularly, an exemplary apparatus of the invention includes a port structure comprising a flexible thermoplastic sleeve heat sealed to any fluid passage means such as a container, and a thermoplastic tube secured to the sleeve to form an extension thereof. Though this thermoplastic tube is hereinafter characterized as "rigid," that term, as used herein, should not be construed synonymously with "brittle," but is intended to describe a structure having sufficient stiffness to maintain its shape under its own weight. The rigid tube has a free end extending beyond the sleeve which is adapted to be joined to the free end of a second rigid tube extending from a sleeve. This second rigid tube and second flexible sleeve comprise a second port structure secured to a second container. Preferably secured near the outer end of each rigid tube is a thermoplastic diaphragm which initially seals off each free end and is subsequently melted open just prior to joining the rigid tubes together in order to effect a sterile connection between the first and second containers.

Sterile joinder of the two containers may be achieved by bringing the first and second rigid tubes into alignment and softening the facing ends thereof, preferably through the application of heat. During this heating process, the thermoplastic diaphragms which previously sealed off each rigid tube are softened, and ultimately melted open. The facing ends of the rigid tubes are then brought into contact and hardened preferably by holding the ends together under a slight pressure while the thermoplastic tubes cool and solidify. Upon solidification, a permanent connection is formed thereby permitting fluid transfer between the two containers.

OBJECTS OF THE INVENTION AND A BRIEF DESCRIPTION OF THE DRAWINGS

It is a primary object of this invention to provide an improved port structure for use with fluid passage means adapted to carry or pass sterile fluid or other biological material.

It is another object of this invention to provide a method for making a sterile connection between two means for passing fluid.

It is a further object of this invention to provide a method for making an improved port structure for use with fluid passage means.

It is still another object of this invention to provide an improved port structure for use with fluid passage means having a flexible thermoplastic sleeve and a rigid thermoplastic tube secured therein.

A feature of this invention provides a method for making a sterile connection between two means for passing fluid requiring minimal skill or training.

Other objects, features and advantages of this invention will become apparent upon reading the following description in conjunction with the accompaying drawings in which:

FIG. 1 is a front view of a container incorporating an exemplary port structure of the invention;

FIG. 2 is an enlarged, fragmented view, taken in perspective of the port structure shown in FIG. 1;

FIGS. 3 and 4 are enlarged front views of the port structure shown in FIG. 1 illustrating the manner in which the port structure is made; and FIGS. 5a, 5b and 5c show two port structures shown in FIG. 1, and illustrate the method by which a sterile connection between two containers is made.

DETAILED DESCRIPTION OF AN EXEMPLARY EMBODIMENT OF THE INVENTION

Referring now to FIG. 1, means for holding or passing fluid or biological material such as a container 10, is shown. Container 10 is preferably formed entirely of two layers of thermoplastic material, heat sealed together to form a watertight seam 11. Disposed about seam 11 of container 10 are any number of ports, three of which are shown in FIG. 1 at 12a, 12b and 12c. Adapted to fit each of ports 12a, 12b and 12c are a corresponding number of port structures represented specifically by reference numerals 17a, 17b and 17c, and represented in general by reference numeral 17.

Port structure 17, shown in greater detail in FIG. 2, is comprised of a flexible thermoplastic sleeve 16 having an inside surface 14 and an outside surface 13 sealed into a container 10 at port 12. Outside surface 13 has greater thermoplastic properties than inside surface 14. This may be accomplished by utilizing a two-ply sleeve, or by coating either inside surface 14 or outside surface 13 with a substance adapted to respectively decrease or increase the thermoplastic properties. In the preferred embodiment, outside surface 13 is a heat sealable coating applid to a polyester film which forms inside surface 14, whereby the application of heat to sleeve 16 enables outside surface 13 to adhere to the inside of container 10 without sealing off inner surface 14.

Port structure 17 further includes a rigid tube 20 having one end 22 secured inside sleeve 16 and a free end 21 extending outside sleeve 16. A thin thermoplastic diaphragm 23 seals off rigid tube 20 at free end 21. Diaphragm 23 has relatively great thermoplastic properties, whereby the application of heat at free end 21 of rigid tube 20 causes the softening and opening of diaphragm 23. A cap 19, adapted to be removably secured over free end 21, is used to protect diaphragm 23 from exposure to gross contamination and accidental puncture. Such a puncture could, of course, expose the interior of port structure 17 to airborne bacteria, thereby making the fluid inside container 10 susceptible to contamination. As a result, it is preferred that cap 19 not be removed until a sterile connection is ready to be made.

FIGS. 3 and 4 illustrate the manner in which port structure 17 is made. More particularly, flexible sleeve 16 is shown in FIG. 3 with inside surface 14 temporarily on the outside, and outside surface 13 temporarily on the inside. Thus, surface 14 may sometimes be referred to herein as a temporary outside surface, and likewise, surface 13 may sometimes be referred to herein as a temporary inside surface.

Still referring to FIG. 3, the free end 21 of rigid tube 20 is inserted deep into sleeve 16 so that end 22 is also captivated thereby. End 22 is adapted to adhere to the temporary inside surface (surface 13) of sleeve 16 to form a water-tight seal 18. The remaining length of sleeve 16, however, is not sealed to rigid tube 20 but is free to move relative thereto.

To complete the construction of port structure 17, sleeve 16 is turned inside out by doubling it back over free end 21 of rigid tube 20, forming a fold which overlaps seal 18. As shown in FIG. 4, free end 21 will then extend outside sleeve 16. Further, the temporary inside surface (surface 13) of sleeve 16 now appears on the outside, and the temporary outside surface (surface 14) now appears on the inside. As shown in FIG. 2, the lower open end of sleeve 16 is then secured inside container 10 to form a watertight connection at port 12.

The manner in which a sterile connection is made between any two fluid passage means having a port structure having an end configuration consisting of a rigid tube sealed off by a thermoplastic diaphragm can now be explained by referring to FIGS. 5a, 5b and 5c. FIG. 5a shows two port structures identified, respectively, by reference numerals 17a and 17b. Port structures 17a and 17b are connected to fluid passage means represented, for exemplary purposes only, as a pair of containers 10a and 10b. Port structures 17a and 17b are respectively comprised of flexible sleeves 16a and 16b, and rigid tubes 20a and 20b. Secured near the end of each rigid tube, at the free end thereof, is a thin thermoplastaic diaphragm such as the one represented by reference numeral 23 in FIG. 2. For reasons explained above, the free end of each rigid tube is protected by caps identified, respectively, by reference numerals 19a and 19b. So that fluid from neither containers 10a nor 10b is prematurely passed, a pair of clamps 29a and 29b is used to close off port structures 17a and 17b, respectively. Said clamping action is, of course, most easily accomplished by clamping across the flexible sleeve rather than across the rigid tube.

To make the sterile connection, caps 19a and 19b are removed, and rigid tubes 20a and 20b are aligned as shown in FIG. 5b. Heat is then applied to the free end of rigid tubes 20a and 20b in any suitable manner, such as through use of a Bunsen burner 30. The heat from Bunsen burner 30 causes the free ends of rigid tubes 20a and 20b to soften until their respective thermoplastic diaphragms melt open. Thereupon, the tube ends are brought into contact and held in position, preferably under slight pressure, while the rigid tubes cool and solidify to form a permanent connection. Thus, upon removal of clamps 29a and 29b, a fluid passage path between containers 10a and 10b is completed as shown in FIG. 5c.

Since the thin thermoplastic diaphragms 23 near the end of rigid tubes 20a and 20b are not opened until the free ends thereof are aligned, softened and ready to be contacted, the interior of the rigid tubes is susceptible to airborne bacteria only for a minute period of time. Even during this period of time, however, the free ends of the rigid tubes are subjected to the sterilizing effects of a high temperature such as the open flame from Bunsen burner 30, thereby assuring a sterile connection. Moreover, since only the simplest manual skills are needed to heat the free ends of the rigid tubes and bring them together, this sterile connection can be made by people having a most minimal amount of training.

Though the embodiment of the invention herein disclosed is preferred, it will be apparent to those skilled in the art that alternatives, variations, and modifications can be devised without departing from the true scope of the invention. It is intended, however, that the appended claims encompass all such alternatives, variations and modifications.

I claim:

1. A method for making a sterile connection between first and second fluid passage means, each of said fluid passage means having a port structure including a thermoplastic tube having a free end sealed off by a thermoplastic diaphragm, comprising the following steps:
   a. aligning each free end of each tube;
   b. heat softening each free end;
   c. melting open each thermoplastic diaphragm;
   d. contacting together each free end of each tube while each free end is in a melted open condition; and
   e. cooling and solidifying the contacting free ends of each tube causing said free ends to be permanently joined.

2. The method set forth in claim 1 wherein said thermoplastic tube is substantially rigid.

3. The method set forth in claim 1 wherein said port structure includes a flexible sleeve secured to each of said rigid thermoplastic tubes.

4. The method set forth in claim 2 further includes the step of closing each port structure prior to step c.

5. The method set forth in claim 4 wherein the closure of each port structure is accomplished by clamping each flexible sleeve.

6. The method set forth in claim 5 further includes the step of unclamping each flexible sleeve after the free ends of each rigid tube are permanently joined.

7. The method set forth in claim 2 further includes sterilizing each free end of each rigid tube.

8. The method set forth in claim 2 wherein steps b. and c. are performed by the application of heat.

9. The method set forth in claim 1 further includes the step of sterilizing each free end.

10. A method for making a sterile connection between first and second fluid passage means, each of said fluid passage means having a port structure including a substantially rigid thermoplastic tube having a free end sealed off by a thermoplastic diaphragm, comprising the following steps:
   a. aligning each free end of each thermoplastic tube;
   b. applying heat to the free end of each of said thermoplastic tubes to soften and sterilize each free end, and to melt open each thermoplastic diaphragm;
   c. contacting together each free end of each thermoplastic tube while each free end is in a melt open condition; and
   d. cooling and solidifying the contacting free ends of each thermoplastic tube causing said free ends to be permanently joined.

11. The method set forth in claim 10 wherein said port structure includes a flexible sleeve secured to said thermoplastic tube.

12. The method set forth in claim 11 further includes the step of closing each port structure by clamping each flexible sleeve prior to step b.

13. The method set forth in claim 12 further includes the step of unclamping each flexible sleeve after the free ends of each thermoplastic tube are permanently joined.

14. The method set forth in claim 10 further includes sterilizing each free end of each thermoplastic tube.

* * * * *